(12) United States Patent
Guelich et al.

(10) Patent No.: US 11,657,911 B2
(45) Date of Patent: May 23, 2023

(54) METHOD FOR FACILITATING COMMUNICATION, DATA ACCESS AND WORKFLOW IN A HEALTHCARE ENVIRONMENT/FACILITY

(71) Applicant: CARE THREAD, INC., Providence, RI (US)

(72) Inventors: Scott Guelich, Riverside, RI (US); Andrew Shearer, Pawucket, RI (US); David Huang, Montclair, NJ (US)

(73) Assignee: Care Thread, Inc., Providence, RI (US)

( * ) Notice: Subject to any disclaimer, the term of this patent is extended or adjusted under 35 U.S.C. 154(b) by 267 days.

(21) Appl. No.: 16/674,768

(22) Filed: Nov. 5, 2019

(65) Prior Publication Data

US 2020/0066401 A1 Feb. 27, 2020

Related U.S. Application Data

(63) Continuation of application No. 14/101,914, filed on Dec. 10, 2013, now abandoned.

(60) Provisional application No. 61/735,084, filed on Dec. 10, 2012.

(51) Int. Cl.
*G16H 40/20* (2018.01)
*G16H 10/60* (2018.01)

(52) U.S. Cl.
CPC .............. *G16H 40/20* (2018.01); *G16H 10/60* (2018.01)

(58) Field of Classification Search
CPC ............................... G16H 40/20; G16H 10/60
USPC ......................................................... 705/2–3
See application file for complete search history.

(56) References Cited

U.S. PATENT DOCUMENTS

| 7,313,529 | B2 | 12/2007 | Thompson |
| 7,451,096 | B2 | 11/2008 | Rucker |
| 3,036,911 | A1 | 10/2011 | Bellon et al. |
| 8,412,539 | B2 | 4/2013 | Srinivasan |

(Continued)

FOREIGN PATENT DOCUMENTS

| EP | 1679648 A1 | 7/2006 |
| WO | 03105062 A2 | 12/2003 |
| WO | 2008144676 A2 | 11/2008 |

OTHER PUBLICATIONS

"Def: A New Variable in Truck Fleets", Work Truck, www.worktruckonline.com, Jan./Feb. 2010.

*Primary Examiner* — Michael Tomaszewski
(74) *Attorney, Agent, or Firm* — Adler Pollock & Sheehan P.C.

(57) ABSTRACT

A method and system of facilitating communication within a healthcare environment is disclosed. The healthcare environment has a directory of providers and a patient census system having patients and patient events. The method and system include a database server configured and arranged to receive and store patients and patient events from the patient census system and providers from the directory, the providers automatically mapped to patients based on predetermined criteria. Patient events are recorded in the patient census system and automatically pushed to the providers mapped to the respective patient in real-time. Preferably, the patient events are pushed to mobile device carried by providers, wirelessly and in real-time. Providers may manage, create and assign patient events via the mobile device, which assigned providers receive and may act on or complete.

16 Claims, 9 Drawing Sheets

(56) References Cited

U.S. PATENT DOCUMENTS

| | | | |
|---|---|---|---|
| 2003/0074222 A1* | 4/2003 | Rosow | G16H 10/60 |
| | | | 705/2 |
| 2004/0034550 A1* | 2/2004 | Menschik | G06F 16/68 |
| | | | 705/3 |
| 2004/0204963 A1* | 10/2004 | Klueh | G06Q 10/10 |
| | | | 705/2 |
| 2005/0075904 A1 | 4/2005 | Wager et al. | |
| 2006/0063563 A1 | 3/2006 | Kaurman | |
| 2006/0282302 A1 | 12/2006 | Hussain | |
| 2007/0239484 A1* | 10/2007 | Arond | G16H 40/20 |
| | | | 705/2 |
| 2009/0147940 A1 | 6/2009 | Graves et al. | |
| 2009/0313046 A1 | 12/2009 | Badgett et al. | |
| 2010/0017231 A1* | 1/2010 | Galbraith | G16H 50/20 |
| | | | 715/764 |
| 2010/0069043 A1 | 3/2010 | Khawand | |
| 2010/0131482 A1 | 5/2010 | Linthicum et al. | |
| 2010/0198614 A1 | 8/2010 | Chopra et al. | |
| 2010/0305970 A1 | 12/2010 | McLaren et al. | |
| 2010/0305972 A1 | 12/2010 | McLaren et al. | |
| 2011/0307284 A1 | 12/2011 | Thompson et al. | |
| 2012/0059669 A1 | 3/2012 | Whittenburg et al. | |
| 2012/0136673 A1* | 5/2012 | Presley | G16H 40/20 |
| | | | 705/2 |
| 2012/0209654 A1 | 8/2012 | Romagnino et al. | |
| 2012/0278094 A1 | 11/2012 | Kovacevic et al. | |
| 2012/0323591 A1 | 12/2012 | Bechtel et al. | |
| 2014/0136223 A1* | 5/2014 | Phillips | G06Q 10/10 |
| | | | 705/2 |
| 2014/0180711 A1* | 6/2014 | Kamen | G16H 70/40 |
| | | | 705/2 |

\* cited by examiner

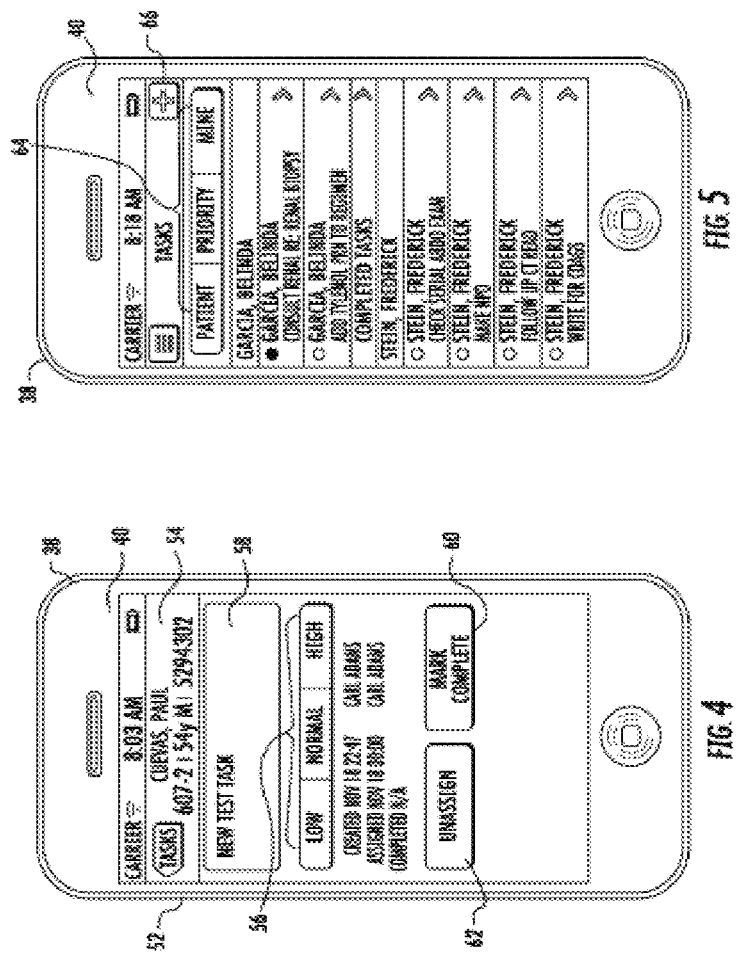

METHOD FOR FACILITATING COMMUNICATION, DATA ACCESS AND WORKFLOW IN A HEALTHCARE ENVIRONMENT/FACILITY

CROSS-REFERENCE TO RELATED APPLICATION

This application is a Continuation of U.S. application Ser. No. 14/101,914, filed Dec. 10, 2013, which claims priority to earlier filed U.S. Provisional Application Ser. No. 61/735,084, filed Dec. 10, 2012, the contents of which are incorporated herein by reference.

BACKGROUND OF THE INVENTION

1. Field of the Invention

The present patent document relates generally to communications systems, and more particularly to a communication system optimized for data access and workflow management in a healthcare facility.

2. Background of the Related Art

Communications and patient management in a medical facility can prove to be daunting. The prior art suffers a number of problems. For instance, locating and paging a specific care team member is inefficient. Communication between healthcare providers taking care of the same patient is also an inconvenient, time-consuming process.

Finding the specific provider is also time-consuming. Providers must often first identify the person they are looking for (who fulfills a specific role in the patient's current care) via an online or operator-assisted directory. Then, they must call a pager number and subsequently wait for the contacted person to return the page via phone. This process can often take many minutes or hours.

Coordination of work in progress and "hand-offs" of this work from one provider or institution to another are also non-trivial tasks in patient care. Providers often do not know when plans are made, changed, or completed, and may not be aligned or agree with them. Team members may also divide work for a particular patient among different members of the team, and this division may change throughout the work shift. These may be communicated verbally, written on paper, or passed from person to person in an ad-hoc format (such as an Excel spreadsheet file), all of which are prone to loss or error. Miscommunication during hand-offs between providers have been found to be responsible for a large proportion of medical errors.

Furthermore, supervising physicians and team members may want to track the status and evolution of these working notes throughout a work shift in real time, which is difficult to do given current tools and processes.

Further complicating matters, nurses may be interrupted during critical location based tasks. There is evidence in the medical literature that interruptions of nurses during specific tasks leads to increased errors and patient harm. In particular, interruptions of nurses during administration of critical medications has been shown to cause errors that may lead to poorer patient outcomes. Therefore, there is a need to minimize interruptions to nurses that are in the process of a task deemed critical.

Another problem in the prior art is the slow dissemination of information.

Responding quickly to changes in patient status is important for providing optimal care. However, the process of informing members of the care team about a patient's latest lab or radiology results, changes in medications, and/or room locations can be slow. There is often a lag between when such a change or update occurs and when pertinent members of the care team are informed. For example, providers often have to access a computer workstation to check the electronic records system at regular intervals to find out if a new lab or radiology result is available in the system. This is an inefficient use of time by this provider. Also, there is a time lag between when the new lab or radiology result has appeared in the system and when this result is checked by the provider; the length of delay depends on when and how often the provider checks the system for new results. Changes in medications, staffing, and room locations also often do not get conveyed to the pertinent care team members in a timely fashion which can lead to delayed patient care.

Another problem in the prior art is the inability to respond to alerts/messages while a provider performs certain procedures. For instance, during routine care of patients, providers must perform certain procedures from time to time that require either the provider's full concentration/engagement or require the provider to be completely sterile/gloved for the duration of the procedure. During such procedures, it is preferred in most cases for the provider to minimize interruptions. If the procedures require sterile gloves, it is inconvenient for the medical team member to have to touch a non-sterile object during the middle of a procedure because he must "scrub out" and then "scrub in" again which can be an inefficient use of time.

Therefore, there is a perceived need in the industry for a system that can manage resources and disseminate critical patient care information in a timely manner. Furthermore, there is a need for a system that can manage resources in a manner that optimizes a location, priority, and patient to available resources, yet also minimizes interruptions of nurses during critical patient care tasks.

SUMMARY OF THE INVENTION

The present invention solves the problems of the prior art by providing a system optimized for team-based, patient-centered, real-time mobile communications.

The system maintains a dynamic, real time list of health care team personnel associated with a particular patient (accessible via desktop or mobile). Members of the care team can be contacted directly and more efficiently because their identity and association with the patient is known immediately through the system's communication system. Moreover, if the care team member who is the target of communication has an enabled mobile device, this person can be contacted immediately.

The system maintains a collection of structured or unstructured notes associated with the patient that can be created, modified and/or viewed by multiple members of the team taking care of a patient. In addition to the associated patient, each note may include metadata such as a priority level, time/date created, time/date completed, name of creator, and/or assignee(s) and/or completer as well as other data. A patient may be associated with multiple notes.

Furthermore the system provides for a mode to prevent interruption during critical patient care tasks. Specifically, mobile devices used in the system feature a "No Interrupt"

mode that takes effect when the device is within range of one or more location marking devices such as an RFID or Bluetooth LE device.

The system further provides an update system that pushes new information such as new lab or radiology results, medication changes, staffing changes and room changes, to a mobile device or computer viewing the interface as soon as this information is available in the medical data system. Care team members can set instant alerts to sound/vibrate the moment an anticipated change occurs so that a pertinent change is brought to a team member's attention immediately.

When a care team member is in the middle of a procedure that requires full engagement or sterile gloves and receives an alert (either a system alert, self-programmed alarm, or communication from other user) from his device, this feature allows the user to physically nudge his device (sensed by the accelerometer) with his arm/elbow/leg/body to silence the alert. Different patterns of bumping or nudging the mobile device can be recognized by the mobile device.

BRIEF DESCRIPTION OF THE DRAWINGS

These and other features, aspects, and advantages of the present invention will become better understood with reference to the following description, appended claims, and accompanying drawings where:

FIG. 4 shows a screenshot of a task creation screen for an application running on a mobile device;

FIG. 5 shows a screenshot of a task management screen for an application running on a mobile device;

DESCRIPTION OF THE PREFERRED EMBODIMENT

Figure 1:
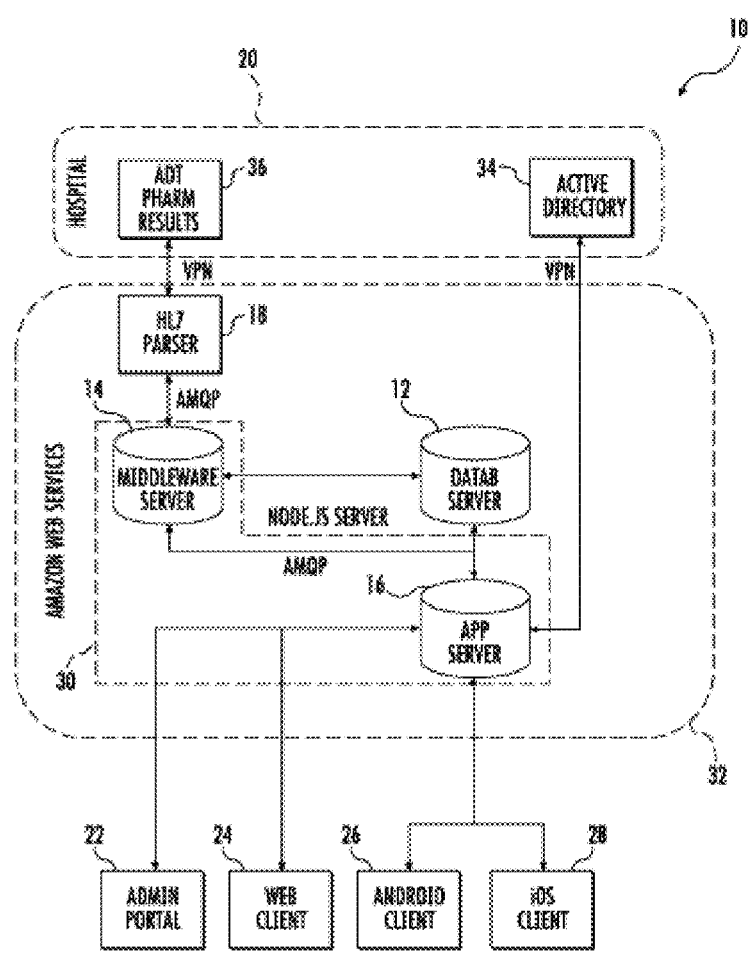
FIG. 1 shows a diagram of the system of the method for facilitating communication, data access, and workflow in a healthcare environment/facility.

Referring now to FIG. 1, a diagram of an embodiment of the system is shown generally at 10. The central piece of the system is a database server 12. Multiple databases may be used to store patient-provider information, such as a patient-team mapping database, patient task database, and a patient updates database, in order to optimize efficiency, provide redundancy, and manage resources of the system, as is known in the art. The database server 12 may be relational or a non-relational database.

It is envisioned that the system 10 may be implemented using any software, written in any programming language for any operating system, on any computer hardware as necessitated by the processing demands placed on the system. The specific examples described herein are for clarity, but it is to be understood that they are examples only and the system 10 may be adapted to use different computer hardware and written or designed for use in different software environments and components. The system 10 may run on a dedicated computer server or run on a virtual machine. Furthermore, the system 10 may be programmed to run on multiple computer servers as needed for scalability. Computer hardware generally includes one or more processors having one or more processing cores, one or more optional coprocessors, random access memory, and storage, which may be a solid state device or one or more hard disks. The storage may be internal or external as desired. The computer hardware may be built from general purpose components or custom designed as desired. Software running aspects of the system described herein may be adapted to be embedded in firmware or run as applications within a general purpose operating system on general purpose computer hardware as desired.

As used herein, the terms "facility", "organization", "clinic" and "hospital" may be used interchangeably.

A middleware server 14 that facilitates real-time messaging connects to the database server 12 and reads and writes data to the database server 12. This middleware server 14 notifies an application server 16, described further below, when data requiring real-time notification changes. An example of data that requires real-time notification is a text message sent from one user to another. The middleware server 14 may use a message bus such as AMQP to coordinate these notifications. Other technology, such as JMS, Redis, XMPP, may also be used.

An HL7 Parser 18 translates data from the hospital's clinical systems 20 via the middleware server 14 to the database server 12, serving as a data conduit. The HL7 Parser 18 may send parsed data to the middleware server 14 via AMQP, but using AMQP is not necessary protocol.

An application server 16 communicates transactions between the database 12, middleware server 14 and clients 22, 24, 26, 28, described further below. Note that the middleware server 14 and application server 16 can be a single server with internal components that provide the described functionality. For instance, a Node.js server 30 may be used to process such transactions. Other application servers may also be used. Moreover, multiple instances of the middleware server 14 and application server 16 may be spawned to provide redundancy, manage and balance system resources, and manage overall transaction load and throughput, as desired. The application server 16 is a front-end to the system and provides internet communications services to the clients 22, 24, 26, 28. Clients 22, 24, 26, 28 may interact with the system 10 through mobile device applications, such as an iOS client 28 or Android client 26. Alternatively, clients may use a web browser 24 through the mobile device or personal computer. Administrative functions may also be performed through an Admin Portal 22.

The core functions 32 of the entire system 10 may be built using virtual servers, such as Amazon Web Services or Microsoft Azure, to maximize scalability.

The system 10 is typically hosted off-site from the healthcare organization, and is integrated with the organization's internal clinical and/or administrative systems 20 through either a secure VPN or another secure communication method. It may also be hosted on-site. For authentication, the system may use its own user database, a hospital's Active Directory or LDAP service 34, a single sign-on system (SSO), or a custom integration with a different existing authentication infrastructure in order to avoid forcing users to maintain another password. A healthcare organization's providers may be determined by reference to the authentication system.

The system 10 may also integrate with one or more clinical systems 36 through data feeds, API access, and/or database access. Feeds send a series of events over time (e.g., a new patient was admitted, a medical order was changed, etc.) most often formatted according to the HL7 standard for health information and technology systems.

One of the feeds the system may rely on comes from a healthcare organization's ADT ("Admission, Discharge, Transfer") system, which manages a hospital's patient census. The patient's identification and particulars, such as name, medical record number, location (unit, room, bed, etc.), basic demographics (age, gender), primary care physician, etc. may be determined. The ADT system sends a stream of events such as when a patient is admitted, discharged, transferred between departments, and when they change rooms, to the system, which are stored in the database server.

Optionally, the following clinical feeds may be received as well in order to provide clinicians using the system the latest results for each patient and summarize these events in the Activity Feed, described further below. In particular, a pharmacy feed (for starting/modifying/discontinuing medications), a laboratory feed (for identifying new pending studies, available study results), a radiology feed (for identifying new pending studies, available study results), a reports feed (including textual notes and reports) and a vitals feed (for gathering vital signs) may be obtained from the healthcare provider.

As the clinical information is intended for quick reference and not long-term archiving, storage may be limited to a customer-defined time period, such as only preserving the last seven days of these results. The connection between the healthcare organization's data sources and the HL7 Parser 18, middleware server 14, and database 12 may be two-way, where data is received from the facility's systems 20, changes are made within system 10 by users (via a mobile device or computer terminal) or according to rules, and the results are pushed back to the database server 12; one-way from the hospital systems 20, where the database server 12 receives data from the facility's systems 20 but does not allow changes; one-way from the database server 12, where data generated within database server 12 is sent to the facility's systems 20; or separate, where data may be created and maintained entirely within the system 10 and are not pushed back into the organization's clinical systems 36.

Care Team Mapping

Figure 2B:
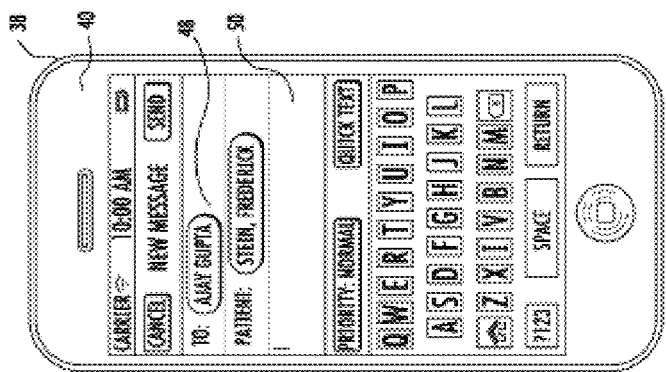
FIG. 2b shows a diagram of an application running on a mobile device, such as a smartphone implementing initiating communication with another Care Team member.
Figure 2A:
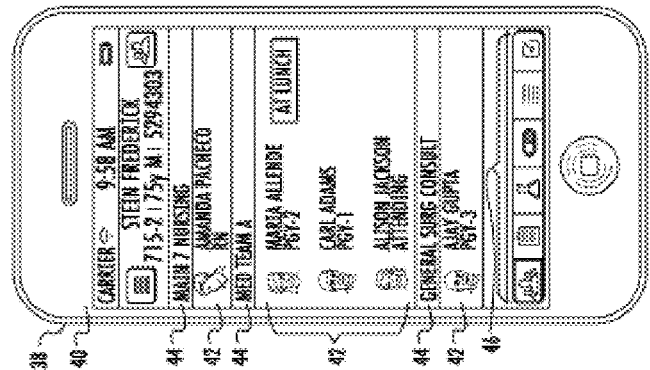
FIG. 2a shows a diagram of an application running on a mobile device, such as a smartphone implementing a patient search feature.

Referring to FIGS. 2a and 2b, an example mobile device 38 running a client application 40 is shown. In FIG. 2a a listing of providers 42 is shown sorted by team 44. The client application 40 may include additional buttons 46 (or icons) for quick navigation to the directory, and to view activity feeds, such as pharmacy feed, a laboratory feed, a radiology feed, a reports feed, a vitals feed, and to view task lists assigned to that particular provider. In FIG. 2b, the user has selected a provider ("Ajay Gupta") 48 to send a direct message to, and an input box 50 is provided to compose the direct message. The user could select multiple providers 42 or even an entire team 44 to send a direct message to. In particular, the mobile device 38 could be an iPhone brand smartphone running a client application 40 programmed for iOS. However, one skilled in the art could create a mobile application 40 suitable to operation on any number of mobile devices, running any mobile operating system.

Figure 3:
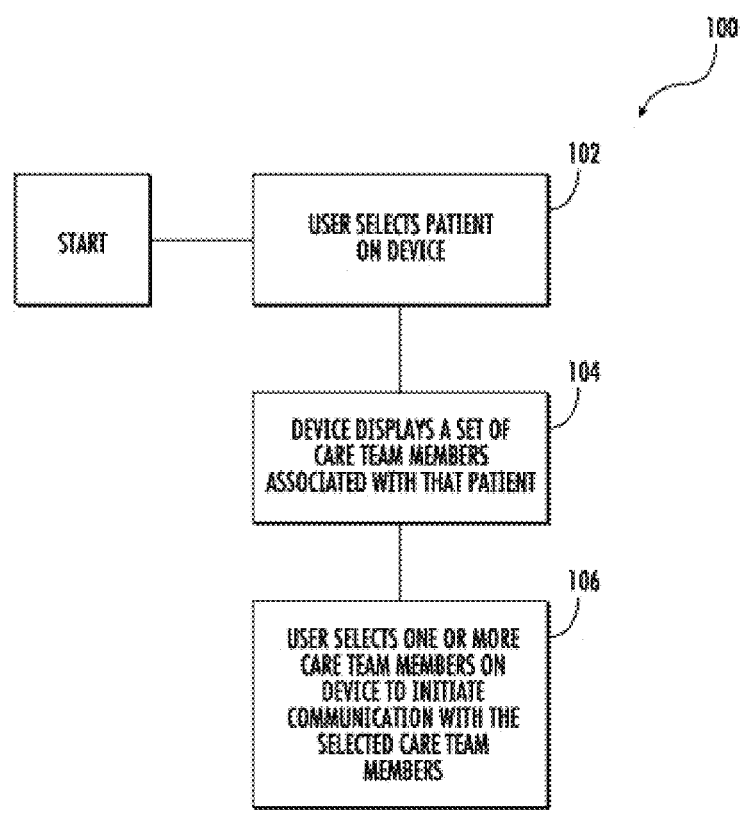
FIG. 3 is a flowchart illustrating a process of initiating communication with another Care Team member.

The system 10 maps individual providers caring for each patient, making it easier for providers to quickly identify other members of the care team in order to improve the speed and efficiency of communication. This information can also be shared with patients and patient family members, either on a display panel in the patient's room or on a secure patient portal via one of the clients 24, 26, 28. FIG. 3 shows the steps of selecting the patient in order to view other Care Team members associated with that patient generally at 100. In a first step 102, the provider selects a patient on the client application 40 on the mobile device 38 or via a web client 24 running on a personal computer or other device capable of running a web browser. In a second step 104, the application displays a set of care team members associated with that patient. In a third step 106, the provider then selects one or more care team members from the list to initiate communication.

Referring back to FIGS. 2a and 2b, providers may also search for other providers as well using a provider's characteristics included in a directory. Selecting a provider's name presents an interface for choosing a communication technique. Selecting the option for secure text messaging opens a message composer with that (recipient) provider's name and the patient's name location, age/gender, and medical record number already populated (selecting the button at top-right with two profiles allows the user to select multiple recipients from the team).

Basic Care Team Implementation

The system 10 receives a real-time stream of data from the healthcare organization's patient census system (ADT), which provides the system with critical information such as when a patient has been admitted, discharged, transferred to another service, or when a patient changes rooms. In a hospital setting, the ADT system typically associates a patient with two providers: the Attending of Record (AOR) and Primary Care Physician (PCP). The PCP is the patient's primary doctor outside the hospital, and the AOR is the physician to whom the patient was admitted in the hospital.

Unfortunately, the AOR in many cases does not accurately represent the physician caring for a patient at any point in time. Many hospitals assign the AOR when the patient is admitted and then never update it unless the patient is transferred to another service, even though other physicians may care for the patient at night and the daytime physician may rotate from day to day or week to week. ADT does not normally track additional physicians (such as residents at an academic center), specialist consultants (such as the surgical consultant shown above), or nurses.

The system therefore relies on both a combination of algorithms and the providers themselves to map Care Teams. Patients are assigned to groups based on the following: [0053] Units: each patient is associated with a nursing unit by ADT. [0054] AOR: although the AOR may not be accurate, we know which services each physician is associated with and can build a lookup-table. So we know that any patient admitted to, e.g. "Allison Jackson", must be admitted to the Medicine service (and specifically Med Team A), even if "Allison Jackson" is no longer in the hospital.

Starting when providers first log into the system at the start of their shift, they are able to view and (with appropriate permissions) update the list of patients that they are caring for. The list of patients may be specific to the provider, or may incorporate a list of patients shared with a larger team, depending on access controls. To add more patients (if allowed by access controls), providers can browse by location to see the patients organized by units, which is primarily useful for nurses who care for patients grouped together by room number. Or they can browse by service, which is primarily useful for physicians (who are assigned to "Med Team A", for example). Or they can search by an arbitrary query. For both nurses and physicians, users can default to displaying the unit/service they viewed the last time they were logged in, and for physicians the selected patient list is preserved from the last time they logged in because they are likely to be caring for the same patients.

We use the concept of "organizational teams" to help share patient lists across providers and shifts. ("Med Team A", "Surgery Consult", and "ICU Nurse Station" are examples of organizational teams.)

Each organizational team is associated with a set of patients.

The patients are determined by one or more of the following, according to configuration specific to the organizational team: patient rules set for the organizational team (typically based on criteria for one or more field values in the ADT feed); integration with external systems that may already maintain this information; or manual addition or removal of patients by users through the application software or by administrators through the admin portal.

Providers belong to zero, one, or more organizational teams. They inherit the patient lists of those teams.

Depending on access controls, providers are permitted to join only a subset of all defined organizational teams. The rules may be attached to the definition of the team (which may be set for the organizational team, the provider, and/or the provider's currently selected role), providers may be permitted only to Roles. Each provider has a current role, such as "Charge Nurse", "Nurse", "Hospitalist", "Resident", "Intern", etc., within each organizational team of which the provider is a member. This role is visible to other users. The role may be selected by the user, typically when adjusting their organizational team membership when starting a shift, from a shortlist of available roles, limited to the intersection of roles available due to user configuration, organizational team configuration, and information received from external systems (when available). For example, a user may be configured by the administrator to be allowed only the "Nurse" or "Charge Nurse" roles, whereas a particular organizational team may be defined by an administrator to allow only a "Nurse" or "Consultant" role. The provider would only be able to join that organizational team with a "Nurse" role. In this case, there's only one choice, which is a common outcome: these constraints will sometimes bypass the need for the provider to explicitly choose a role at all, by forcing one. Access control and scoping for other operations may be performed based on the provider's role. Patients also may be allowed to use the system, and they act just like providers with a special "patient" role.

Typically, when providers join an organizational team, they inherit the full patient list associated with it. However, if allowed by the administrator, they may be able to select a subset of the patients associated with the organizational team.

Organizational teams may be arranged in a hierarchy, allowing for easier choices, and mirroring the organizational hierarchy of the healthcare institution.

Organizational teams based on rules automatically update as circumstances change. If one of the patients no longer meets the criteria for membership in the team's patient list (typically due to an external change received on the ADT feed, such as transferring the patient to a different unit, discharging the patient, or changing the patient's attending of record), the patient is removed by the system. If another patient is changed to match the criteria, the patient is added. Changes are pushed to the client applications in real time if the clients are viewing any screens that depend on the organizational team's patient list.

Organizational teams may be configured to include rules that automatically include other teams, presenting a merged patient list. For example, a "Med Night Float" team could be configured to present a patient list that was the union of the patients lists for "Med Team A," "Med Team B," and "Med Team C".

When viewed onscreen, a provider's patient list that includes patients inherited from more than one source team may be grouped by the name of the source team.

Changes to the patient lists of any of the source teams automatically cause the patient list of the merged team to update accordingly. Changes appear in real time, and are pushed to users who are viewing the teams, or any other screens including dependent data.

Providers may, if allowed by access rules, be able to add ad-hoc patients that appear only on their patient list, not on a team patient list.

Integration with the healthcare organization's authentication and/or directory systems may be used to retrieve providers' names, roles, allowed units/services, and/or profile photos. (Information not retrievable from an organization's own systems can usually be entered or uploaded manually within the administrative panel.) Once a provider is associated with a group of patients, we can then show that provider's information as part of that patient's care team.

Providers' membership in organizational teams allows the system to display all the providers associated with each organizational team, including a screen that shows all of the logged-in provider's teammates.

Additionally, providers are able to update their availability (i.e. their presence) by indicating whether they are on/off shift and whether they are unavailable (with an optional custom status message if unavailable). The patient's care team lists all providers "On Team" associated with the patient, along with the real-time status of each provider (available, unavailable, custom status, off teams).

Notes

"Notes" are a shorthand way of referring to textual information associated with a patient and made available for creation, viewing and/or editing through the system. Users may enter notes in a semi-structured format to convey information about the patient to other providers, typically in order to coordinate "hand-offs" of care between the providers or services. There are a configurable set of note fields and allowance for multiple types of notes, some of which may be associated with structured metadata, such as creation date, author, priority, and status, in addition to the patient. Users may enter any desired information into different types of notes, such as plans of care, hand-off notes, task/to-do items, announcements, replies, questionnaire responses (a type of structured note), and other communications. Once a user edits a note, the updated content is made available in real time to others who have access. Updates are pushed immediately to others currently viewing the screens on which the notes appear. Significantly, notes are not necessarily part of the medical record, nor are necessarily saved back to an EMR system-they can be used akin to temporary working notes that used to be written on paper and discarded when no longer needed, such as after a hand-off.

Notes created in the system are associated with a patient (and thus the patient's name, location, age/gender, and medical record number). Additionally, the system tracks certain events for each note, which contain both a timestamp and an associated user (or care team member), including creation and editing.

Although this field is not normally shown to the user, each piece of user-editable information is associated with a scope that determines which providers can see it. Each institution can determine which combination of provider roles share the same scope. For example, Hospital A may decide that nurses, primary doctors, specialist doctors, case managers, discharge planners, etc. all see the same notes, which may be especially appropriate for a small hospital. In this case there is only one scope and all notes (and providers) share the same scope. However, Hospital B may decide that primary doctors have one list; specialist doctors have another list; and nurses, case managers, and discharge planners share a third list. This may be more appropriate at a large teaching hospital where there are multiple residents serving as primary doctors and as specialist doctors. In this case, users in the different scopes have independent sets of notes, even when they view the same patient.

Notes are not only shared simultaneously across multiple providers, they are also shared across time (i.e. personnel shift changes). As mentioned above, each note is associated with a patient, so any provider associated with a patient will see all the notes for that patient (insofar as the note is within that provider's scope). This ensures that notes are consistent across provider shift changes or even transfers between different inpatient medical services.

FIG. 4 shows a note or task creation screen on the client application 40 running on the mobile device 38. Tasks may also be created through a web portal 24 on a device capable of running a web browser or through the admin portal 22. Tasks are connected to a patient and the patient information is displayed in the top bar 54 of the task creation screen 52. Tasks may be assigned a priority via a number of icons or selectors 56, a text entry field 58 is provided for describing the task. Alternatively, predefined tasks may be assigned to the text entry field 58 avoid unnecessary repetition and errors in entering task descriptions. Tasks may be marked complete by any provider assigned to the task via an icon 60. Tasks may be assigned to one or more providers or an entire care team via another icon 62, which brings up the list of available providers in the Active Directory or the current care team members that the current provider belongs to.

Figure 6:
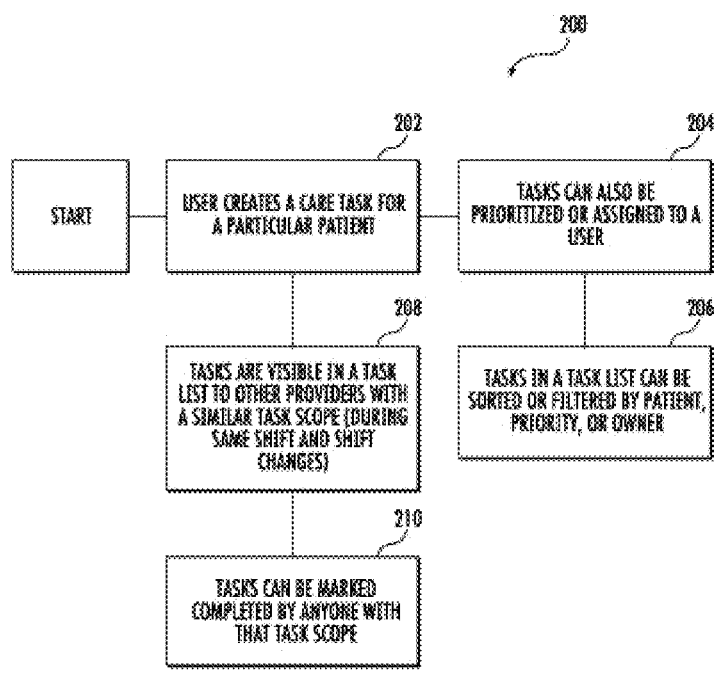
FIG. 6 shows a flowchart of an example process of creating and managing tasks in the system.

The process of creating a task is described in FIG. 6 at 200. In a first step 202, the user creates a care task for a particular patient. Optionally, the provider may assign a priority or assigned to other providers to the task at a second step 204. Tasks may be sorts and filtered by different fields, such as by patient, by priority of by owner, in a third step 206. Tasks are visible to other providers with a similar task scope, i.e. during the same shift and shift changes, or part of the same care team, in a fourth step 208. In a fifth step 210, tasks may be completed by any provider within the same task scope.

Each provider can view the notes or tasks within their scope for each of their patients as shown in FIG. 5. Additionally, the provider can see all of their notes and tasks across all the patients they are associated with. The notes and tasks may be sorted and filtered as mentioned above via predefined filters, such by patient, by priority or by owner via icons 64. This view is unique to each provider who will likely have a different combination of patients. The provider my create a new note or task from this screen by pressing a new task creation icon 66, which invokes the task creation screen described above and shown in FIG. 4.

Activity Feed

Figure 7A:
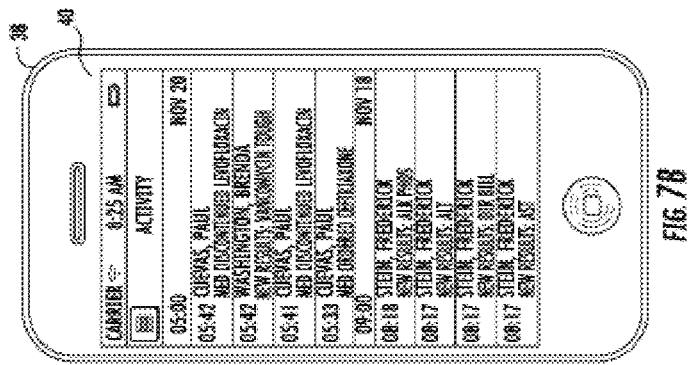
FIG. 7a shows a screenshot of a mobile device with an activity feed for an individual patient.
Figure 7B:
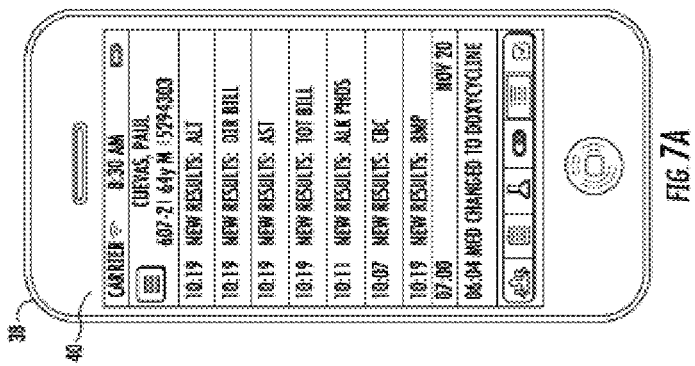
FIG. 7b shows a screenshot of a mobile device with an activity feed for all patients associated with that care team member.
Figure 8:
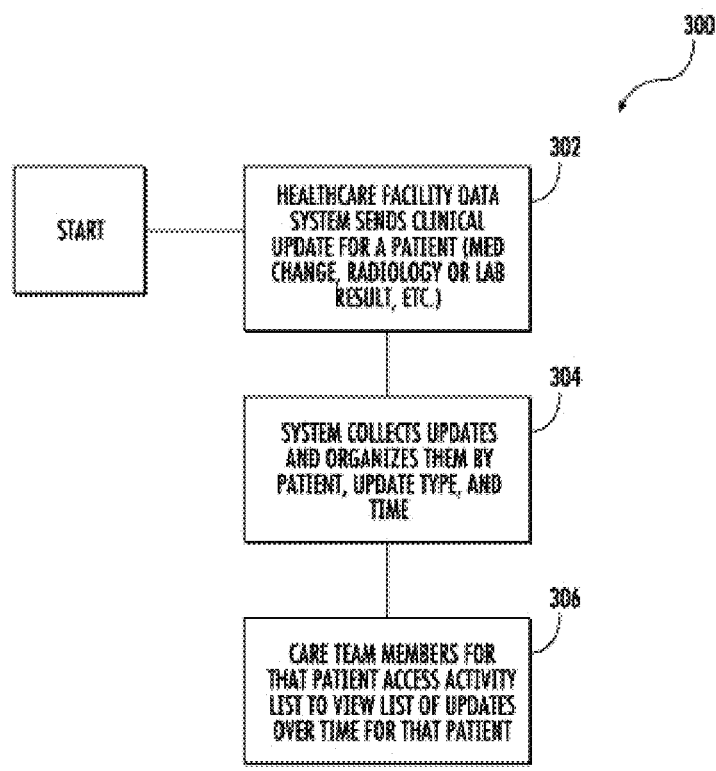
FIG. 8 shows a flowchart of a process of collecting patient information and updating care team members.

Referring to FIGS. 7a and 7b, two versions of the real time Activity Feed are shown. FIG. 7a shows the results for a single patient and FIG. 7b shows results across all patients that are associated with a provider (i.e. logged in user). FIG. 8 shows a flowchart 300 of the process of receiving and viewing patient activity in real time. In a first step 302, the system 10 sends a clinical update to a patient, such as a medical condition change, radiology or laboratory results, etc. In a second step 304, the system 10 collects updates and organizes them by patient, update type and time. In a third step 306, care team members for that patient access activity list to view the list of updates over time for that patient.

The Activity Feed is analogous to a Twitter feed that displays pertinent clinical results for patients, pushed to a web browser or mobile device application as it becomes available. Throughout the day, a provider needs to keep track of multiple pending or final studies for each of their patients and follow-up on these results. Typically this requires going to a computer, logging into an electronic record system, selecting each patient's record, and looking at the lab/radiology/medication screens, and trying to determine what has changed.

The system's real-time Activity Feed gives providers a convenient way to monitor updates over time right from their mobile device or a web browser. An Activity Feed can display, but is not limited to, the following activities and/or updates: [0084] New lab results [0085] New radiology reports [0086] Medications started/changed/discontinued [0087] New patients admitted/discharged [0088] Patient room changes [0089] Changes to the care team associated with a patient No-Hands Response Referring to FIG. 9, as alluded to previously, when a care team member is in the middle of a procedure that requires full engagement or donning sterile gloves, and receives an alert (either a system alert, self-programmed alarm or communication from other user) on his or her mobile device 38. This feature allows the user to physically nudge his mobile device 38 (sensed by the accelerometer) with his arm/elbow/leg/body to silence the alert. Different patterns of bumping or nudging the mobile device 38 can be recognized by the mobile device 38. Depending on the specific pattern of nudging/bumping, a different pre-programmed status update can be relayed to the system 10 or other users/providers. For example, if a user/provider receives a text message alert from his/her device, he may use one pattern of bumping/nudging the device to update his status to "busy but will respond in five minutes or less." A different pattern of bumping/nudging may indicate "occupied for the next half hour, please contact someone 2nd call in case of emergency". Because the provider can respond to a message without the use of hands, the provider saves valuable time from having to de-glove and rescrub/sanitize themselves in order to respond. At a minimum, the feature is convenient for providers that merely have their arms or hands full with no convenient place to set things down in order to respond to the message.

Figure 9:
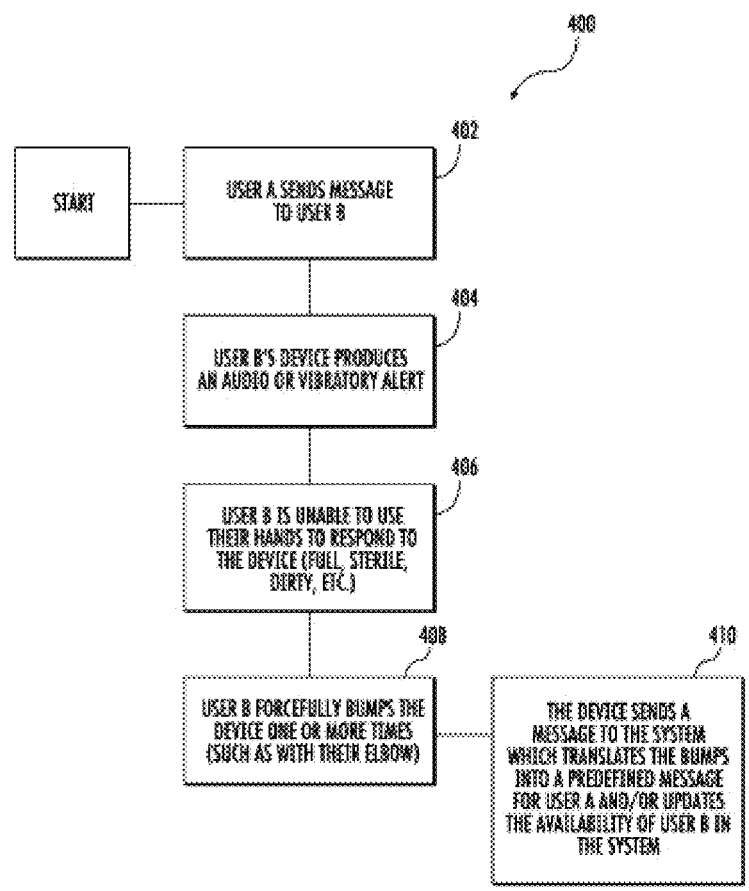
FIG. 9 shows a flowchart of a process of no-hands responding to alerts sent to a mobile device.

This process is illustrated in FIG. 9 at 400. At step 402, User A sends a message to User B. At step 404, User B's device produces an audio of vibratory alert. At step 406, User B is unable to use their hands to respond to the incoming message on the mobile device 38. At step 408, User B forcefully bumps the device one or more times to silence the alert. At step 410, the client application 40 on the mobile device 38 sends a message to the system 10 which translates the one or more bumps into a predefined message for User A and/or updates the availability of User B in the system 10.

Do not Disturb

Figure 10:
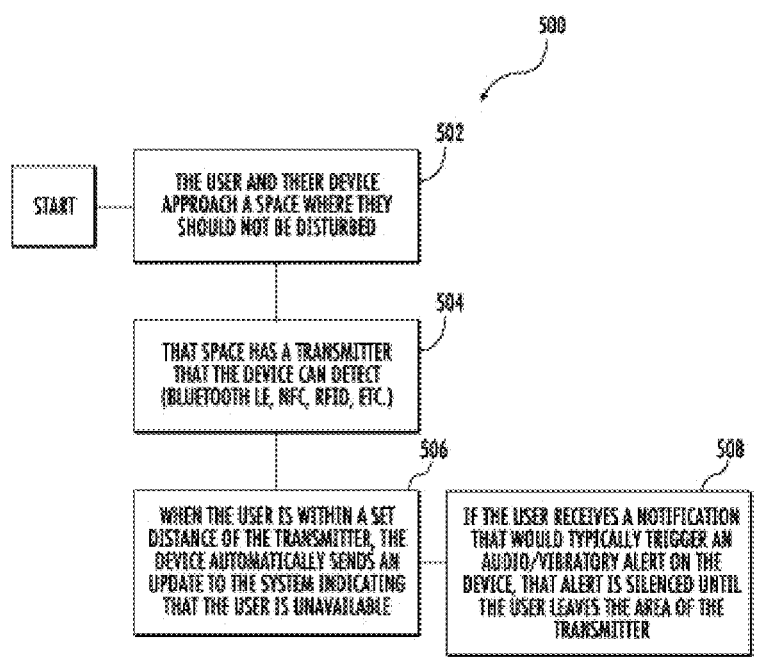
FIG. 10 shows a flowchart of a process of do not disturb zones, creating a distraction-free environment where critical patient tasks are being performed.

Referring to FIG. 10, the system provides for a mode to prevent interruption during critical patient care tasks. Specifically, mobile devices used in the system feature a "No Interrupt" mode that takes effect when the device is within range of one or more location marking devices such as an RFID or Bluetooth LE device. Using the appropriate signaling technology, the mobile devices detect when they are within close range of a signaling device (or set of devices) that indicate a "No Interrupt Zone." If the "No Interrupt" mode of the mobile device is activated, specific types of alerts (such as communication messages or self-created alarms) will not sound or vibrate until the user has moved out of the "No Interrupt Zone." Earlier alerts will be delivered to the user, no alerts are lost. By limiting alerts during critical patient care tasks, medical errors can be reduced as distractions to the provider will be reduced.

This process is illustrated in FIG. 10 at 500. At step 502 the user (carrying their mobile device 38) approaches a space where they should not be disturbed. At step 504, the space is provided with a transmitter that the mobile device can detect. At step 506, when the user is detected as being within a set distance of the transmitter, the client application 40 on the mobile device 38 automatically sends an update to the system indicating that the user is unavailable and should not be disturbed. At step 508, if the user receives a notification that would typically trigger an audio or vibratory alert on the mobile device 38, that alert is silenced until the user leaves the are of the transmitter.

Optionally, the provider may manually set their mobile device to a "Do Not Disturb" setting to limit alerts. The system may override a provider's manual setting for certain emergency events. Also, the manual setting may be disabled if an inordinate amount of time has lapsed, as determined by the system administrators.

Therefore, it can be seen that the system and method described herein provides a unique solution to the prior art problems of managing and allocating resources in a healthcare environment, matching providers and patients with relevant clinical information. The system and method further provides an ability to push out data and communications to providers in real time, tasks and activity updates in order to maximize the use of the provider's time and minimize response time to patient's needs. Furthermore the system minimizes medical errors by providing "no interruption zones" in order to prevent providers from being distracted during critical patient care.

Therefore, it can be seen that the present invention provides a unique solution to the problem of providing a communication system in a hospital/health care environment that facilitates communication between providers concerning critical patient care tasks, yet reduces distraction, resulting in reduced rate of medical errors.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A system comprising:
   a hospital clinical system comprising an admission-discharge-transfer system and an authentication server;
   a core functions system communicatively linked to the hospital clinical system, the core functions system comprising a database server, a HL7 parser and a Node.js server; and
   a plurality of clients communicatively linked to the core functions system, each client of the plurality of clients having a client device,
   wherein the admission-discharge-transfer system is configured to send a stream of events to the database server for storage,
   wherein the events are selected from the group consisting of an event indicating when a patient is admitted, an event indicating when the patient is discharged, an event indicating when the patient is transferred between departments, and an event indicating when the patient changes rooms,
   wherein the admission-discharge-transfer system is configured to send the stream of events to the plurality of clients only when the client device is not within range of one or more location marking devices, and
   wherein the core functions system is configured to receive feedback from the plurality of clients based on tactile patterns directed at the client device.

2. The system of claim 1 wherein the Node.js server comprises:
   a middleware server configured to interact with the database server, the application server and the HL7 parser; and
   an application server configured to interact with the database server, the authentication server and the plurality of clients.

3. The system of claim 2 wherein the plurality of clients includes one or more of an admin portal client, a web client, an Android client, and an iOS client.

4. The system of claim 3 wherein the database server comprises patient-provider information.

5. The system of claim 4 wherein the patient-provider information comprises:
   a patient-team mapping database;
   a patient task database; and
   a patient updates database.

6. The system of claim 5 wherein the middleware server is configured to store real-time messaging connects to the database server.

7. The system of claim 6 wherein the middleware server is further configured to and read and write data to the database server.

8. The system of claim 7 wherein the middleware server is further configured to notify the application server when data requiring real-time notification changes.

9. The system of claim 8 wherein the HL7 Parser is configured to translate data from the hospital clinical systems to the to the database server via the middleware server.

10. The system of claim 9 wherein the application server is configured to communicate transactions between the database sever server, the middleware server and the plurality of clients.

11. The system of claim 10 wherein the link between the core functions system and the hospital clinical system is a virtual private network (VPN).

12. The system of claim 11 wherein the middleware server is further configured to receive a pharmacy feed from the admission-discharge-transfer system.

13. The system of claim 11 wherein the middleware server is further configured to receive a laboratory feed from the admission-discharge-transfer system.

14. The system of claim 11 wherein the middleware server is further configured to receive a radiology feed from the admission-discharge-transfer system.

15. The system of claim 11 wherein the middleware server is further configured to receive a reports feed from the admission-discharge-transfer system.

16. The system of claim 11 wherein the middleware server is further configured to receive a vitals feed from the admission-discharge-transfer system.

* * * * *